United States Patent
Ito et al.

(10) Patent No.: US 10,162,027 B2
(45) Date of Patent: Dec. 25, 2018

(54) MAGNETIC RESONANCE IMAGING APPARATUS AND IRRADIATION MAGNETIC FIELD DISTRIBUTION MEASUREMENT METHOD

(71) Applicant: HITACHI, LTD., Tokyo (JP)

(72) Inventors: Kosuke Ito, Tokyo (JP); Masahiro Takizawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1196 days.

(21) Appl. No.: 14/350,224

(22) PCT Filed: Oct. 31, 2012

(86) PCT No.: PCT/JP2012/078088
§ 371 (c)(1),
(2) Date: Apr. 7, 2014

(87) PCT Pub. No.: WO2013/069513
PCT Pub. Date: May 16, 2013

(65) Prior Publication Data
US 2014/0253121 A1   Sep. 11, 2014

(30) Foreign Application Priority Data

Nov. 8, 2011 (JP) ................. 2011-244740
Oct. 24, 2012 (JP) ................. 2012-234424

(51) Int. Cl.
*G01R 33/44* (2006.01)
*A61B 5/055* (2006.01)
(Continued)

(52) U.S. Cl.
CPC ............ *G01R 33/443* (2013.01); *A61B 5/055* (2013.01); *G01R 33/246* (2013.01); *G01R 33/3415* (2013.01); *G01R 33/5659* (2013.01)

(58) Field of Classification Search
CPC ............ G01R 33/5659; G01R 33/246; G01R 33/443; G01R 33/3415; A61B 5/055
See application file for complete search history.

(56) References Cited

U.S. PATENT DOCUMENTS

2007/0255128 A1   11/2007   Nistler
2007/0299332 A1   12/2007   Ikeda
(Continued)

FOREIGN PATENT DOCUMENTS

JP   2007-283104   11/2007
JP   2008-5899     1/2008
(Continued)

OTHER PUBLICATIONS

International Search Report in PCT/JP2012/078088.

*Primary Examiner* — Rishi Patel
(74) *Attorney, Agent, or Firm* — Cooper & Dunham LLP

(57) ABSTRACT

To obtain the irradiation magnetic field distribution of each channel of a multichannel transmission RF coil at high speed, for multiple channels which are all or some of the channels of the transmission coil, an image is acquired by irradiation with one channel or a combination of two or more channels, an irradiation magnetic field distribution upon irradiation with all of the multiple channels is acquired, and the irradiation magnetic field distribution of each channel is calculated using the acquired irradiation magnetic field distribution of all of the multiple channels and the phase difference calculated from the image of each channel and the image of all of the multiple channels.

16 Claims, 16 Drawing Sheets

(51) Int. Cl.
   *G01R 33/24*   (2006.01)
   *G01R 33/3415*   (2006.01)
   *G01R 33/565*   (2006.01)

(56) References Cited

U.S. PATENT DOCUMENTS

| | | | | |
|---|---|---|---|---|
| 2008/0100292 | A1* | 5/2008 | Hancu | G01R 33/10 |
| | | | | 324/307 |
| 2010/0239142 | A1 | 9/2010 | Dannels et al. | |
| 2011/0026799 | A1* | 2/2011 | Nehrke | G01R 33/246 |
| | | | | 382/131 |
| 2012/0161766 | A1* | 6/2012 | Harvey | G01R 33/5612 |
| | | | | 324/309 |
| 2012/0163692 | A1* | 6/2012 | Harvey | G01R 33/5659 |
| | | | | 382/131 |
| 2013/0207653 | A1* | 8/2013 | Ito | G01R 33/246 |
| | | | | 324/309 |

FOREIGN PATENT DOCUMENTS

| | | |
|---|---|---|
| JP | 2010-221026 | 10/2010 |
| WO | WO2010/113062 | 10/2010 |
| WO | WO2011/155461 | 12/2011 |
| WO | WO2012/060192 | 5/2012 |

* cited by examiner

MAGNETIC RESONANCE IMAGING APPARATUS AND IRRADIATION MAGNETIC FIELD DISTRIBUTION MEASUREMENT METHOD

TECHNICAL FIELD

The present invention relates to a magnetic resonance imaging apparatus (hereinafter, referred to as an MRI apparatus), and in particular, to an MRI apparatus which includes a function of measuring an irradiation magnetic field distribution of an irradiation coil configured to irradiate a high-frequency magnetic field onto an object.

BACKGROUND ART

An MRI apparatus is an apparatus which measures a nuclear magnetic resonance signal generated by applying a high-frequency magnetic field pulse to an object in a state where the object is disposed in a homogenous magnetostatic field and reconstructs an image of the object by an arithmetic operation of the nuclear magnetic resonance signal. A magnetic field generation device is used to generate a high magnetic field as the magnetostatic field in which the object is disposed, thereby obtaining an image having a high SN.

In recent years, with the development of a superconducting magnet, a high-magnetic field MRI apparatus which can realize a high magnetic field equal to or greater than 3 T has been in widespread use. In the high-magnetic field MRI, while a high SN is obtained, there is a problem in that irregularity occurs in an image during abdominal imaging or the like. One of the factors of irregularity is inhomogeneity of the magnetic field distribution (B1 distribution) of a high-frequency magnetic field pulse (also referred to as a transmission RF pulse), which excites an atomic spin in a tissue of an object. In general, since the resonance frequency of a high-frequency magnetic field for excitation is in proportion to magnetostatic field strength, it is necessary for the high-magnetic field MRI to irradiate a magnetic field at a higher frequency than a prior high-frequency magnetic field. In this case, the wavelength of the high-frequency magnetic field inside a living body has a scale comparable to the size of the living body (in particular, abdomen). For this reason, the phase of the high-frequency magnetic field changes depending on the position inside the living body, and the change appears as image irregularity.

As a technique for solving inhomogeneity of the high-frequency magnetic field, RF shimming is known. In the RF shimming, a transmission RF coil having multiple channels is used, and the strength and phase of an RF pulse provided to each of the channels is controlled separately, thereby reducing inhomogeneity of the B1 distribution. In order to determine the strength and phase of an RF pulse provided to each channel, the B1 distribution of each channel is required for each object and each imaging region, and various measurement methods of the B1 distribution are suggested.

A general method, which measures the B1 distribution, is called a Double Angle method (DAM) and measures B1 by an arithmetic operation of an image using an RF pulse at an arbitrary flip angle and an image using an RF pulse at a double flip angle (NPL 1). Furthermore, a method which takes the ratio of an image acquired immediately before pre-pulse application and an image acquired without pre-pulse application to compute the B1 distribution (NPL 2), or a method (Actual Flip Angle method: AFI) which acquires image data using a set of pulse sequences having different TR with RF pulses at the same flip angle and calculates the B1 distribution using the signal ratio of image data and the TR ratio (NPL 3) is suggested.

CITATION LIST

Non Patent Literature

[NPL 1] Insko E K, Bolinger L, "Mapping of the Radiofrequency Field" Journal of magnetic resonance. Series A 1993; 103: 82-85

[NPL 2] H-P. Fautz, M. Vogel, P. Gross, A. Kerr, and Y. Zur, "B1 Mapping of Coil Arrays for Parallel Transmission", Proc. Intl. Soc. Mag. Reson. Med. 16 (2008) 1247

[NPL 3] Yarnykh V L, "Actual Flip-Angle Imaging in the Pulsed Steady State: A Method for Rapid Three-Dimensional Mapping of the Transmitted Radiofrequency Field", Magn. Reson. Med. 2007; 57: 192-200

SUMMARY OF INVENTION

Technical Problem

In the above-described RF shimming, although it is necessary to measure the irradiation magnetic field distribution for each channel of the transmission RF coil, when the above-described method is applied to measure the irradiation magnetic field distribution for each channel, a magnetic field distribution measurement increases in proportion to the number of channels. When the irradiation magnetic field distribution is measured for each channel, since there are a number of regions having small magnetic field strength in a region of interest, high-precision measurement is difficult.

Accordingly, an object of the invention is to obtain the irradiation magnetic field distribution of each channel of a multi-channel transmission RF coil at high speed. Another object of the invention is to prevent degradation of precision when measuring the irradiation magnetic field distribution for each channel.

Solution to Problem

In order to solve the above-described problem, in the invention, to calculate the irradiation magnetic field distribution of each channel in an MRI apparatus with a transmission coil having two or more channels, for multiple channels which are the whole or a part of the transmission coil, an image is acquired by irradiation with one channel or a combination of two or more channels, an irradiation magnetic field distribution upon irradiation with all of the multiple channels is acquired, and the irradiation magnetic field distribution of each channel is calculated using the acquired irradiation magnetic field distribution of all of the multiple channels and the phase difference calculated from the image of each channel and the image of all of the multiple channels.

Advantageous Effects of Invention

According to the invention, since it should suffice that a comparatively time-consuming irradiation magnetic field distribution measurement is made once for the entire transmission coil, and the irradiation magnetic field distribution of each channel can be obtained by an arithmetic operation between the measured irradiation magnetic field distribution and image data, it is possible to significantly reduce the required measurement time for the irradiation magnetic field distribution measurement.

BRIEF DESCRIPTION OF DRAWINGS

FIG. 5(a) shows a case where the number of channels is two, and FIG. 5(b) shows a case where the number of channels is equal to or greater than three.

FIG. 14(a) shows computation in Step S143, and FIG. 14(b) shows computation in Step S105.

FIGS. 15(a) and 15(b) are diagrams showing the B1 distribution of channels C1 and C2 obtained in an example, and FIGS. 15(c) and 15(d) are diagrams showing the B1 distribution of channels C1 and C2 obtained in a comparative example.

DESCRIPTION OF EMBODIMENTS

Figure 1:
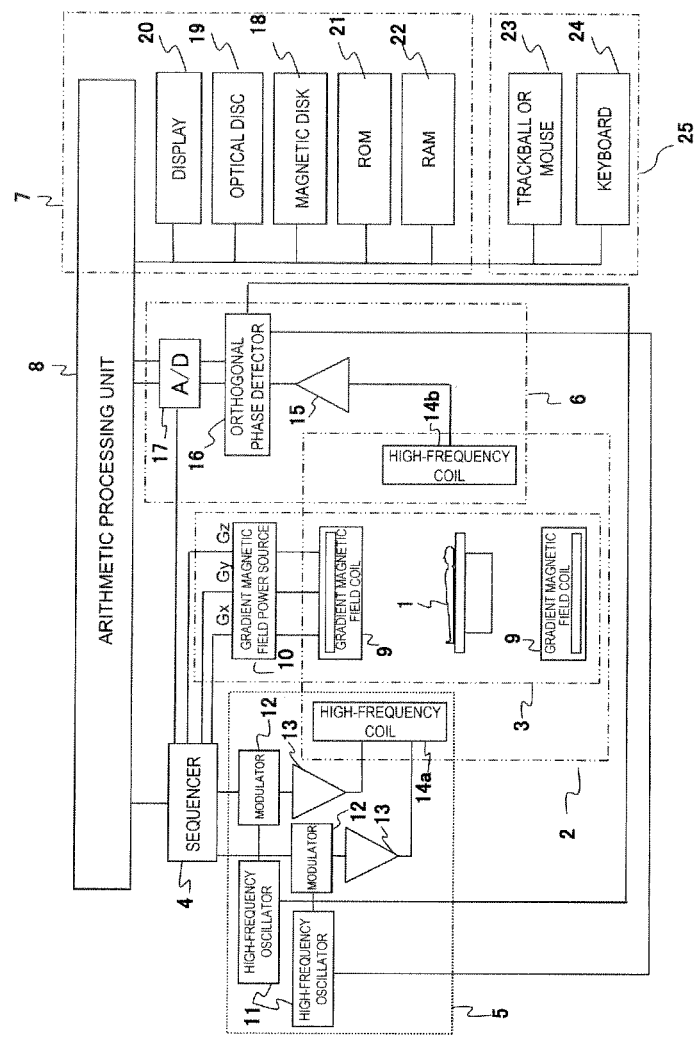
FIG. 1 is a diagram showing the overview of an MRI apparatus to which the invention is applied.

An MRI apparatus of this embodiment includes an imaging unit (2 to 6) which includes a transmission unit (5) configured to irradiate a high-frequency magnetic field onto an object (I) and a reception unit (6) configured to receive a nuclear magnetic resonance signal from the object, an arithmetic unit (7, 8) which processes the nuclear magnetic resonance signal acquired by the reception unit and performs an arithmetic operation including image reconstruction, and a control unit (4, 8) which controls imaging by the imaging unit. The transmission unit includes a transmission coil (14a) having two or more channels.

The control unit has an image acquisition sequence (301, 302) in which, for multiple channels which are the whole or a part of the transmission coil, a partial irradiation image is acquired by irradiation with one channel or a combination of two or more channels, and an irradiation magnetic field distribution measurement sequence (310) in which an irradiation magnetic field distribution upon irradiation with all of the multiple channels is measured. The image acquisition sequence may include an image acquisition sequence (303) in which an image is acquired by irradiation with all of the multiple channels.

The arithmetic unit includes a first irradiation magnetic field distribution calculation unit which calculates the irradiation magnetic field distribution of all of the multiple channels using data acquired in the irradiation magnetic field distribution measurement sequence, and a second irradiation magnetic field distribution calculation unit which calculates the irradiation magnetic field distribution of each channel of the multiple channels using multiple pieces of image data acquired in the image acquisition sequence and the irradiation magnetic field distribution of all of the multiple channels calculated by the first irradiation magnetic field distribution calculation unit.

Specifically, the second irradiation magnetic field distribution calculation unit calculates the irradiation magnetic field distribution of each channel using the phase of the image (partial irradiation image) obtained by irradiation of some channels, the phase of the image (overall image) of all channels, and the irradiation magnetic field distribution calculated by the first irradiation magnetic field distribution calculation unit. When there is the image acquisition sequence (303) in which irradiation with all of the multiple channels is performed, the image of all channels may be the image acquired in the image acquisition sequence, or an image in which multiple partial irradiation images are synthesized.

The image acquisition sequence and the irradiation magnetic field distribution measurement sequence are preferably the same pulse sequence. With the same pulse sequence, it is possible to cancel inhomogeneity of the magnetostatic field in the respective pieces of image data in an arithmetic operation between the pieces of image data.

The irradiation magnetic field distribution measurement sequence is, for example, one of the pulse sequences based on a double angle method (DAM), a fitting method, and an actual flip angle method (AFI), or a pulse sequence based on a multi-TI method. When the pulse sequence based on the multi-TI method is introduced, for example, the first irradiation magnetic field distribution calculation unit solves a simultaneous equation for each pixel of image data obtained by each of multiple signal acquisition sequences, thereby obtaining irradiation magnetic field strength of each pixel and calculating the irradiation magnetic field distribution.

The image acquisition sequence may take various forms. In regard to the execution order of the image acquisition sequence and the irradiation magnetic field measurement sequence, the image acquisition sequence may be executed immediately before the irradiation magnetic field measurement sequence, or the image acquisition sequence may be executed after TR of the irradiation magnetic field measurement sequence.

Hereinafter, an embodiment of an MRI apparatus of the invention will be further described referring to the drawings. In all drawings for describing an embodiment of the invention, the parts having the same functions are represented by the same reference numerals, and repetitive description will be omitted.

FIG. 1 is a block diagram showing an embodiment of an MRI apparatus to which the invention is applied. The MRI apparatus includes a magnetostatic field generation unit 2, a gradient magnetic field generation unit 3, a transmission unit 5, a reception unit 6, a signal processing unit 7, a sequencer 4, and a central processing unit (CPU) 8.

The magnetostatic field generation unit 2 generates a homogenous magnetostatic field in a space where an object 1 is placed, and has a permanent magnet type, normal conducting type or superconducting type magnetostatic field generation source (not shown). The magnetostatic field generation source is arranged so as to generate a homogenous magnetostatic field in a direction orthogonal to the body axis of the object 1 in a vertical magnetic field type and to generate a homogenous magnetostatic field in the body axis direction in a horizontal magnetic field type.

The gradient magnetic field generation unit 3 has gradient magnetic field coils 9 which apply a gradient magnetic field in an orthogonal three-axis direction of X, Y, and Z as the coordinate system (static coordinate system) of the MRI apparatus, and a gradient magnetic field power source 10 which drives the respective gradient magnetic field coils. The gradient magnetic field power source 10 of the respective coils is driven in accordance with a command from the sequencer 4 described below, thereby applying desired gradient magnetic fields Gx, Gy, and Gz in the three-axis direction of X, Y, and Z. Depending on a way to apply a gradient magnetic field, it is possible to selectively excite a slice to be image of the object, and to add positional information to an echo signal generated from an excited region.

The sequencer 4 is a control unit which repeatedly applies a high-frequency magnetic field pulse (hereinafter, referred to as "RF pulse") and a gradient magnetic field pulse in a predetermined pulse sequence, operates under the control of the CPU 8, and transmits various commands necessary for data acquisition of a tomographic image of the object 1 to the transmission unit 5, the gradient magnetic field generation unit 3, and the reception unit 6.

The transmission unit 5 irradiates an RF pulse onto the object 1 in order to generate nuclear magnetic resonance in a nuclear spin of an atom constituting a biological tissue of the object 1, and has high-frequency oscillators 11, modulators 12, high-frequency amplifiers 13, and a transmission-side high-frequency coil (transmission coil) 14a. In this embodiment, a transmission coil has multiple feed points (channels) and is configured to adjust the strength and phase of a high frequency to be supplied. Multiple high-frequency oscillators 11, modulators 12, and high-frequency amplifiers 13 are provided corresponding to the respective channels. In FIG. 1, although a case where two feed points are provided is described, the number of feed points is not limited to two.

The RF pulse output from each of the high-frequency oscillators 11 is amplitude-modulated by each of the modulators 12 at the timing according to a command from the sequencer 4, and the amplitude-modulated RF pulse is amplified by each of the high-frequency amplifiers 13 and supplied to the high-frequency coil 14a arranged close to the object 1, whereby the RF pulse is irradiated onto the object 1. The timing from the sequencer 4 and the modulation by each of the modulators 12 are controlled in conformance with the measurement result of the B1 distribution described below.

The reception unit 6 detects the echo signal (NMR signal) emitted by nuclear magnetic resonance of the nuclear spin constituting the biological tissue of the object 1, and has a reception-side high-frequency coil (reception coil) 14b, a signal amplifier 15, an orthogonal phase detector 16, and an A/D converter 17. The response NMR signal of the object 1 induced by electromagnetic waves irradiated from the transmission coil 14a is detected by the reception coil 14b arranged close to the object 1, is amplified by the signal amplifier 15, and is divided into two orthogonal systems of signals by the orthogonal phase detector 16 at the timing according to a command from the sequencer 4. Each signal is converted to a digital quantity by the A/D converter 17 and transmitted to the signal processing unit 7.

In FIG. 1, although a configuration in which the transmission high-frequency coil 14a and the reception high-frequency coil 14b are provided separately has been described, a configuration in which a single high-frequency coil (including multiple coils) is used for both transmission and reception may be made.

The signal processing unit 7 has a CPU 8, an external storage device, such as an optical disc 19 or a magnetic disk 18, which performs display and storage of various kinds of data processing and processing results, and a display 20 having a CRT or the like. If data from the reception unit 6 is input to the CPU 8, the CPU 8 executes processing, such as signal processing or image reconstruction, displays the tomographic image of the object 1 as the processing result on the display 20, and records the tomographic image in the magnetic disk 18 or the like of the external storage device.

Figure 2:
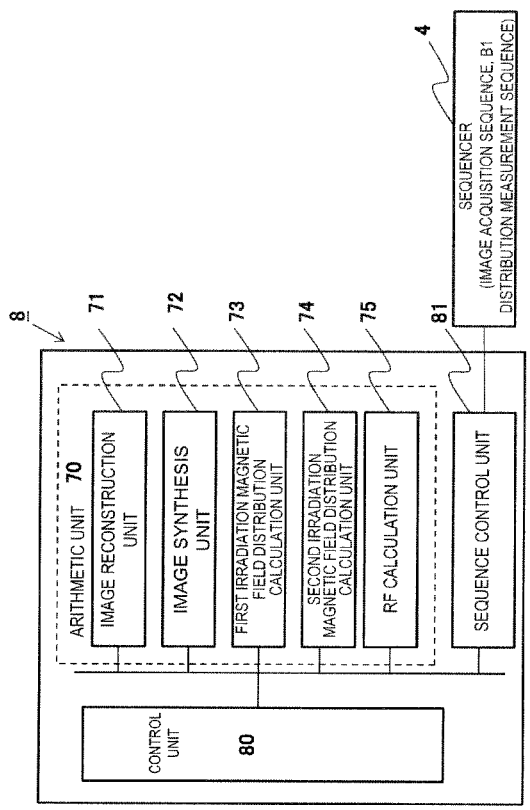
FIG. 2 is a functional block diagram of a control unit which is common to a first embodiment to a fourth embodiment.

As shown in FIG. 2, the CPU 8 has a function as a control unit 80, which controls the respective elements of the apparatus, in addition to a function as an arithmetic unit 70 of the signal processing unit 7, and a sequence control unit 81 which is one of the functions of the control unit 80 executes various pulse sequences through the sequencer 4. A pulse sequence is embedded as a program in advance. In this embodiment, in addition to a pulse sequence (image acquisition sequence) for obtaining the image of the object, a B1 distribution measurement sequence for measuring a high-frequency magnetic field distribution (B1 distribution) by the transmission coil is provided.

The signal processing unit 7 (arithmetic unit 70) includes an image reconstruction unit 71 which performs an arithmetic operation, such as correction computation or Fourier transformation, on the digitized echo signal to perform image reconstruction, an image synthesis unit 72 which performs image synthesis as necessary, a magnetic field distribution calculation unit (73, 74) which performs computation of the B1 distribution using the measurement result of the B1 distribution measurement sequence acquired in each channel, and an RF calculation unit 75 which performs computation of the phase or amplitude of the high-frequency pulse to be provided to the transmission coil. The control unit 80 controls the phase or amplitude of the high-frequency pulse to be provided to the transmission coil on the basis of the computation result of the RF calculation unit 75.

The magnetic field distribution calculation unit includes a first irradiation magnetic field distribution calculation unit 73 which calculates an irradiation magnetic field distribution upon irradiation with all of multiple channels of the transmission coil, and a second irradiation magnetic field distribution calculation unit 74 which calculates an irradiation magnetic field distribution upon irradiation with some channels of the multiple channels of the transmission coil using the irradiation magnetic field distribution calculated by the first irradiation magnetic field distribution calculation unit 73 and image data created by the image reconstruction unit 71 or the image synthesis unit 72. The RF calculation unit 75 includes a shimming unit which adjusts the phase or amplitude of the high-frequency pulse on the basis of the irradiation magnetic field distribution of each channel calculated by the irradiation magnetic field distribution calculation unit.

The operating unit 25 is provided to input various kinds of control information of the MRI apparatus or control information of processing which is performed by the signal processing unit 7, and has a trackball or mouse 23 and a keyboard 24. The operating unit 25 is arranged close to the display 20, and an operator controls various kinds of processing of the MRI apparatus interactively through the operating unit 25 while viewing the display 20.

In FIG. 1, in the magnetostatic field space of the magnetostatic field generation unit 2 into which the object 1 is inserted, the transmission-side high-frequency coil 14a and the gradient magnetic field coils 9 are arranged so as to face the object 1 in a vertical magnetic field type or so as to surround the object 1 in a horizontal magnetic field type. The reception-side high-frequency coil 14b is provided so as to face or surround the object 1.

Figure 3:
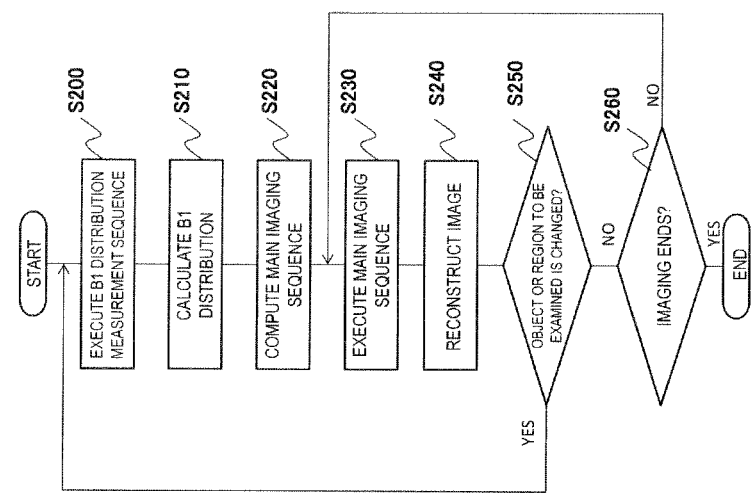
FIG. 3 is a flowchart showing an embodiment of the operation of an MRI apparatus of the invention.

An embodiment of an imaging procedure of the MRI apparatus configured as above is shown in FIG. 3. As shown in the drawing, the image procedure includes execution of a pulse sequence for B1 distribution measurement (S200), calculation of the B1 distribution for each channel using data obtained by the pulse sequence in Step S200 (S210), computation of an imaging sequence (main imaging sequence) for acquiring the image of the object or the like (S220), execution of the main imaging sequence (S230), image reconstruction using data acquired in the imaging sequence (S240), and other determination steps (S250, S260). The pulse sequences which are executed in Steps S200 and S240 are embedded in the sequencer 4, and can set parameters or the like necessary for execution through the operating unit 25 or correct the parameters in accordance with the arithmetic operation result of the CPU (arithmetic unit) 8.

A main feature of this embodiment is the pulse sequence for B1 distribution measurement (S200) and calculation of the B1 distribution using data obtained in the pulse sequence (S210). Hereinafter, this embodiment will be described.

First Embodiment

An image acquisition sequence which is introduced in this embodiment is a pulse sequence in which irradiation with one channel of multiple channels is performed, and is repeated the same number of times as the number of channels while changing the channels for use in irradiation. In this case, the second irradiation magnetic field distribution calculation unit calculates the irradiation magnetic field distribution of each channel using a partial irradiation image acquired for each channel and an overall image.

That is, in this embodiment, in Step S200, for the transmission coil in which the number of channels is n, RF irradiation is performed for each channel to acquire image data, and RF irradiation with all channels is performed to acquire overall image data. Furthermore, the B1 distribution upon RF irradiation with all channels is measured. In Step S210, image data (individual image data) for the number of channels, image data (all irradiation image data) as the whole transmission coil, and the B1 distribution (all irradiation B1 distribution) of the transmission coil as a whole are acquired.

Figure 4:
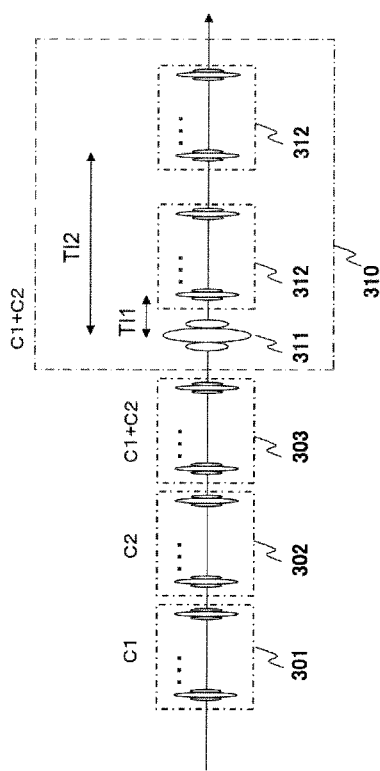
FIG. 4 is a diagram showing a pulse sequence for B1 distribution measurement of a first embodiment.

FIG. 4 shows an example of a pulse sequence which is executed in Step S200 when the number of channels is two. As shown in the drawing, the pulse sequence has a pulse sequence (image acquisition sequence) 301 in which RF irradiation is performed using a first channel C1 to acquire an image, an image acquisition sequence 302 using a second channel C2, an image acquisition sequence 303 using the first and second channels C1 and C2 (all channels) simultaneously, and a pulse sequence 310 for B1 distribution measurement when RF irradiation is performed using all channels (C1+C2) simultaneously. It is preferable that RF irradiation using all channels is QD irradiation.

Although the B1 distribution measurement pulse sequence 310 differs depending on a measurement method, in this embodiment, a pulse sequence based on a method (referred to as a multi-TI method), which obtains the B1 distribution by an arithmetic operation between multiple images having different TI after a pre-pulse, is used. Specifically, after the application of the single pre-pulse 311, multiple image acquisition sequences 312 having different TI (the elapsed time from the application of the pre-pulse to effective TE) are performed. The pre-pulse 311 is, for example, a non-selective RF pulse, and a pulse at a large flip angle, for example, 90 degrees. The multiple image acquisition sequences 312 are executed while the nuclear spin excited by the pre-pulse 311 is not longitudinally relaxed, and multiple pieces of k-spatial data (image data) having different TI are acquired. Here, in order to provide distinction from the image acquisition sequences 301 to 303 which are executed prior to the B1 distribution measurement pulse sequence 310, the sequence 312 is called a signal acquisition sequence.

The multi-TI method solves a simultaneous equation between the multiple pieces of k-spatial data having different TI or performs a matrix operation between the multiple pieces of k-spatial data to calculate the B1 distribution, and at least three pieces of k-spatial data are required for the arithmetic operation. In the embodiment shown in FIG. 4, a case where image data of the image acquisition sequence 303 executed immediately before the pre-pulse 311 and two or more pieces of image data obtained by executing the signal acquisition sequence 312 twice while differing TI after the pre-pulse are used as three or more pieces of k-spatial data has been described. The signal acquisition sequence 312 may be performed three or more times.

It is preferable that the image acquisition sequences 301 to 303 and the signal acquisition sequence 312 are the same type of pulse sequence, and specifically, a gradient echo pulse sequence, in particular, a pulse sequence for reduction in imaging time, in which the repetition time (TR) is short and the flip angle (FA) is small, is preferably used. In the image acquisition sequences 301 to 303, a data set (k-spatial data) which satisfies a single k space is acquired.

The matrix size of k-spatial data which is acquired in the image acquisition sequences 301 to 303 and the signal acquisition sequence 312 may be about 64×64. With this, it is possible to acquire all pieces of k-spatial data in a very short time, specifically, for the measurement time of about 200 ms.

Next, the calculation of the B1 distribution using data obtained in Step S200 will be described.

<Calculation of Overall B1 Distribution>

The B1 distribution upon RF irradiation with all channels is calculated from data obtained in the B1 distribution measurement pulse sequence 310. As described above, as the B11 distribution calculation method by the multi-TI method, a method which solves a simultaneous equation and a method which solves a matrix operation are known, and here, the method by the matrix operation will be described.

First, inverse Fourier transformation is performed on k-spatial data obtained in each of the multiple signal acquisition sequences 312 to obtain image data. When the k-th TI is $TI_k$, the signal strength of a target pixel of an image reconstructed from a signal acquired in a k-th (where k=1, 2, ..., n) signal acquisition sequence after the application of the pre-pulse 311 is provided by Expression (1).

$$S(B1, TI_k) = S_{seq}(1-(1-\cos(B1 \cdot a))\exp(-TI_k/T_1)) \quad (1)$$

In Expression (1), $S_{seq}$ represents signal strength which is determined by a signal acquisition sequence after a pre-pulse, a represents the set flip angle of the pre-pulse, TI represents the time from the application of the pre-pulse until a signal of the k space center is acquired, and T1 represents a longitudinal relaxation time depending on a tissue.

The signal strength of the same target pixel of an image obtained by the image acquisition sequence 303 immediately before the pre-pulse 311 is the same as when a=0 in Expression (1) and is thus provided by Expression (2).

$$S(0,a) = S_{seq} \quad (2)$$

If Expression (1) is divided by Expression (2), and a natural logarithm is taken, as in Expression (3), the natural logarithm can be expressed by a linear combination of $\log(1-\cos(B1\cdot a))$ and $(-TI_k/T_1)$.

$$\log\left(1 - \frac{S(B1, TI_k)}{S_0}\right) = \log(1 - \cos(B1 \cdot a)) - \frac{TI_k}{T_1} \quad (3)$$

If the same computation is performed on images having different TI obtained from the respective signal acquisition sequences, a determinant of Expression (4) is obtained.

$$S = A \cdot X \quad (4)$$

$$S = \begin{pmatrix} W_1 \cdot \log\left(1 - \frac{S(B1, TI_1)}{S_0}\right) \\ W_2 \cdot \log\left(1 - \frac{S(B1, TI_2)}{S_0}\right) \\ W_3 \cdot \log\left(1 - \frac{S(B1, TI_3)}{S_0}\right) \\ W_4 \cdot \log\left(1 - \frac{S(B1, TI_4)}{S_0}\right) \\ \vdots \end{pmatrix}, A = \begin{pmatrix} W_1 & W_1 \\ W_2 & W_2 \cdot \frac{TI_2}{TI_1} \\ W_3 & W_3 \cdot \frac{TI_3}{TI_1} \\ W_4 & W_4 \cdot \frac{TI_4}{TI_1} \\ \vdots \end{pmatrix},$$

$$X = \begin{pmatrix} \log(1 - \cos(B1 \cdot a)) \\ -\frac{TI_1}{T_1} \end{pmatrix}$$

Here, S is a 1×n matrix, A is a 2×n matrix, and X is a 1×2 matrix. $W_i$ (where i=1, 2, 3, . . . , n) represents the weight for each TI, and can be arbitrarily set. A pseudo inverse matrix pinvA of the matrix A is multiplied from left, thereby solving Expression (4) and obtaining B1 as in Expression (5).

$$B1 = \frac{\mathrm{acos}[1 - \exp[(pinvA)_{1i}S_1]]}{a} \quad (5)$$

<Calculation of B1 Distribution of Each Channel>

Inverse Fourier transform is performed on k-spatial data acquired in the image acquisition sequences 301, 302, and 303 to obtain image data of the first channel, the second channel, and all channels. The phase of each pixel is obtained for these pieces of image data. The phase can be calculated from arctangent of a real part and an imaginary part of image data. The phase of a pixel of the first channel (also referred to as the phase of the first channel image) is represented as $\phi 1$, the phase of a pixel of the second channel (also referred to as the phase of the second channel image) is represented as $\phi 2$, and the phase of a pixel of all channels (also referred to as the phase of the all-channel image) is represented as $\phi total$.

Next, the difference ($\phi total-\phi 1$) between the phase of the all-channel image and the phase of the first channel image and the difference ($\phi total-\phi 2$) between the phase of the all-channel image and the phase of the second channel image are obtained. These differences are represented as $\alpha$ and $\beta$. B1 of all channels is obtained by synthesizing the irradiation distribution of the first channel and the irradiation distribution of the second channel, and when the irradiation distribution of each channel is represented by the magnetic field strength T1 and T2 in one pixel, the irradiation distribution can be expressed as a vector (complex number) on a complex plane shown in FIG. 5(*a*). The difference between the phase of the synthesized magnetic field strength (T1+T2) and the phase of the magnetic field strength T1 of the first channel is $\alpha$, and the difference between the phase of the synthesized magnetic field strength and the phase of the magnetic field strength T2 of the second channel is $\beta$.

Figure 5:
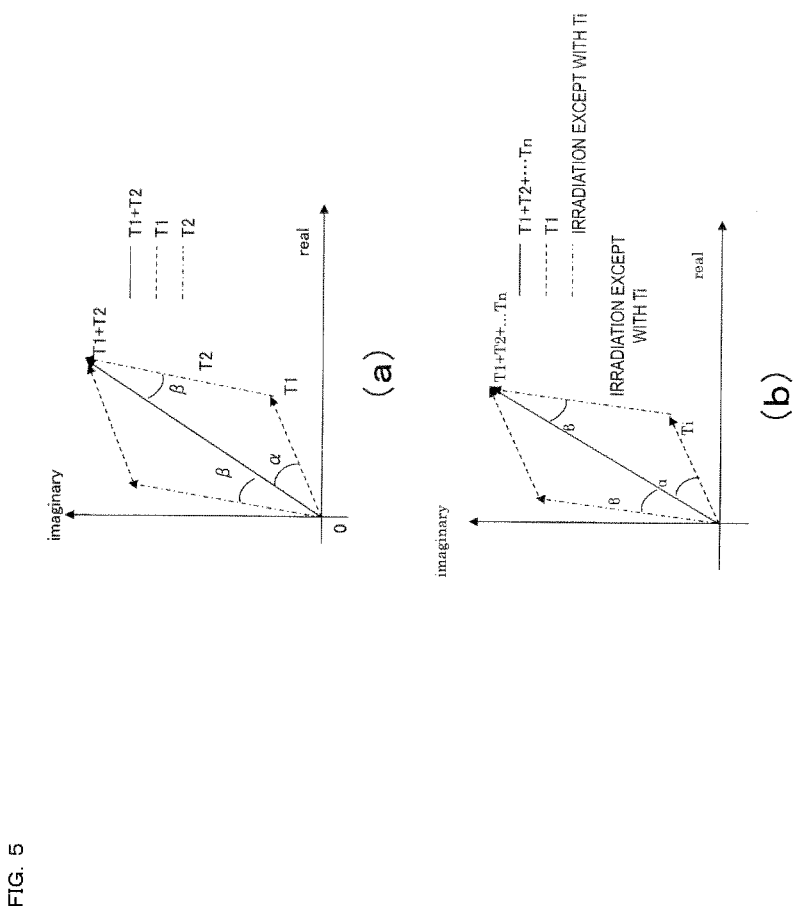
FIG. 5 is a diagram illustrating the concept of B1 distribution calculation in the first embodiment.

In FIG. 5(*a*), since the synthesized magnetic field strength (T1+T2) is obtained as B1 of all channels, the magnetic field strength T1 and T2 of the respective channels which are an unknown can be calculated by Expressions (6) and (7).

$$|T1| = \left|\frac{\sin\beta}{\sin(\alpha-\beta)}\right| |T1+T2| \quad (6)$$

$$|T2| = \left|\frac{\sin\alpha}{\sin(\alpha-\beta)}\right| |T1+T2| \quad (7)$$

This computation is performed for each pixel of image data of the first channel and the second channel, thereby obtaining the B1 distribution of each channel.

According to this embodiment, the image acquisition pulse sequence having a very short data acquisition time and the B1 distribution measurement of only the overall transmission coil are performed, thereby obtaining the B1 distribution of each channel and significantly reducing the B1 distribution measurement time. The B1 distribution measurement uses data of the overall transmission coil having a high signal value, thereby performing high-precision measurement. In particular, it is possible to perform QD irradiation to reduce regions having small B1 as much as possible, thereby improving precision.

If the matrix size of image data is 64×64 and the repetition time TR of the pulse sequence is 5000 ms, although the imaging time when creating the two-channel B1 distribution using the conventional DAM is about 20 minutes, in this embodiment, the imaging time can be reduced to 2.5 seconds.

In the above description, although a case where the number of channels is two has been described, this embodiment can be applied in the same manner even when the number of channels is equal to or greater than three. When the number of channels is n (where n=an integer equal to or greater than three), an image Ic in which an image Ii acquired by irradiation with one channel Ci (where i is 1 to n) and the image acquired by irradiation with each of the rest channels C1 to Cn (excluding Ci) are synthesized by Expression (8) is used.

$$Ic = \sum_{k \ne i} I_k \quad (8)$$

The phases of the respective pixels of the two images are obtained, and the differences from the phase of the image of all-channel irradiation are obtained. Here, if the image Ii of one channel is regarded as the image of the first channel C1 and the synthesized image Ic is regarded as the image of the second channel C2, the relationship shown in FIG. 5(b) is obtained, and the irradiation magnetic field distribution of the channel Ci can be calculated by Expression (6) using the phase differences α and β and the magnetic field strength (T1+T2+ . . . +Tn) of all-channel irradiation. This computation is performed for all channels 1 to n, whereby the B1 distribution of all channels is calculated.

In the foregoing embodiment, although a case where the B1 distribution is calculated using image data obtained in the image acquisition sequence 303 immediately before the pre-pulse 311 and the multiple signal acquisition sequence 312 having different TI after the pre-pulse 311 has been described as the multi-TI method, the simultaneous equation may be solved using image data obtained in the multiple signal acquisition sequences 312 having different TI after the pre-pulse 311 to calculate the B1 distribution. The computation in this case is as follows.

The signals of the images acquired in the multiple signal acquisition sequences 312 having different TI are expressed by Expressions (9) to (11) when TI, 2TI, and 3TI of the signal acquisition sequences 312 are set.

$$S(B1,TI) = S_{seq}(1-(1-\cos(B1 \cdot a))\exp(-TI/T1)) \quad (9)$$

$$S(B1,2TI) = S_{seq}(1-(1-\cos(B1 \cdot a))\exp(-2TI/T1)) \quad (10)$$

$$S(B1,3TI) = S_{seq}(1-(1-\cos(B1 \cdot a))\exp(-3TI/T1)) \quad (11)$$

Here, if X and Y which are defined by Expressions (12) and (13) are used, Expressions (9) to (11) can be rewritten as Expressions (14) to (16).

$$1-\cos(B1 \cdot a) \equiv X \quad (12)$$

$$\exp(-TI/T_1) \equiv Y \quad (13)$$

$$S(B1,TI) = S_{seq}(1-XY) \quad (14)$$

$$S(B1,2TI) = S_{seq}(1-XY^2) \quad (15)$$

$$S(B1,3TI) = S_{seq}(1-XY^3) \quad (16)$$

The simultaneous equations of Expressions (14) to (16) are solved, thereby obtaining X and Y by Expressions (17) and (18) and obtaining B1 from Expressions (17) and (12) (Expression (19)).

$$X = \frac{[S(B1, TI) - S(B1, 2TI)]^3}{[S(B1, 2TI) - S(B1, 3TI)]} \quad (17)$$

$$[\{S(B1, 2TI)\}^2 - S(B1, TI)S(B1, 3TI)]$$

$$Y = \frac{S(B1, 2TI) - S(B1, 3TI)}{S(B1, TI) - S(B1, 2TI)} \quad (18)$$

$$B1 = \frac{\arccos(1-X)}{a} \quad (19)$$

Although the execution time (measurement time) of the pulse sequence for B1 distribution measurement is longer than the multi-TI method, a method other than the multi-TI method, for example, the B1 distribution measurement may be performed by a known double angle method (DAM) or an actual flip angle method (AFI). In case of the DAM, instead of the pre-pulse 311 and the subsequent pulse sequence, images obtained with RF irradiation at an arbitrary flip angle and RF irradiation at a double flip angle are used, and B1 is calculated by an arithmetic operation between these images. In case of the AFI, image data is obtained using a set of pulse sequences having different TR with RF pulses having the same flip angle, and B1 is calculated using the signal ratio of image data and the TR ratio. These methods are described in NPLs 1 and 3 described above, and thus description thereof will be omitted.

Second Embodiment

An image acquisition sequence which is introduced by this embodiment is a pulse sequence in which irradiation with the rest channels excluding one channel of multiple channels is performed, and is repeated the same number of times as the number of channels while changing a channel to be excluded. In this case, the second irradiation magnetic field distribution calculation unit calculates, using the image acquired in the pulse sequence excluding one channel and the overall image, the phase difference between the phase of the image of one channel and the phase of the overall image and calculates the irradiation magnetic field distribution of each channel using the phase difference and the irradiation magnetic field distribution calculated by the first irradiation magnetic field distribution calculation unit.

That is, as in the first embodiment, the pulse sequence for B1 distribution measurement of this embodiment has multiple image acquisition sequences and a B1 distribution measurement sequence. This embodiment has a feature in that, in the B1 distribution computation of each channel, image data upon irradiation with the rest channels excluding one channel is used instead of image data of each channel.

To this end, in this embodiment, in Step S200, the image acquisition sequence is executed by irradiation of the rest channels excluding one channel, instead of irradiation of one channel. That is, in case of the transmission coil in which the number of channels is n, the image acquisition sequence 301 using (n−1) channels excluding one channel is executed n times while changing a channel to be excluded from 1 to n, thereby obtaining n pieces of image data.

As in the first embodiment, the image acquisition sequence is executed using all of the n channels and the multiple signal acquisition sequences are executed after the irradiation of the pre-pulse 311, and finally, n pieces of image data using the (n−1) channels, image data by irradiation with all channels, and the B1 distribution upon irradiation with all channels are obtained. The pulse sequence for obtaining the B1 distribution of all channels is not limited to the multi-TI method using the above-described pre-pulse, and as in the first embodiment, the DAM or AFI may be used.

Next, the B1 distribution of each channel is calculated using image data and the B1 distribution. First, the difference $\alpha_k$ between the irradiation phase $\phi_k$ of a channel k (where k is 1 to n) and the irradiation phase $\phi_{tot}$ upon irradiation with all channels is obtained by Expression (20). The difference $\beta_k$ between the irradiation phase $\phi_{tot}$ upon irradiation with all channels and the irradiation phase $\phi_{-k}$ upon irradiation with the channels other than the channel k is obtained by Expression (21).

$$\alpha_k = \phi_{tot} - \phi_k = \arg\left(\frac{\Phi_{tot}}{\Phi_{tot} - \Phi_{-k}}\right) \quad (20)$$

$$\beta_k = \phi_{tot} - \phi_{-k} = \arg\frac{\Phi_{tot}}{\Phi_{-k}} \quad (21)$$

In Expressions, Φtot represents image data (pixel value) by irradiation with all channels, $\Phi_{-k}$ represents image data (pixel value) by irradiation with the channels other than the channel k, and image data is acquired by the image acquisition sequence.

Figure 6:
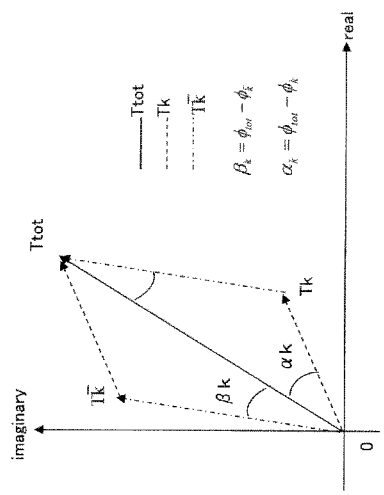
FIG. 6 is a diagram illustrating the concept of B1 distribution calculation in a second embodiment.

As shown in FIG. 6, the relationship among the irradiation strength $T_k$ of the channel k, the irradiation strength T-k of the channels other than the channel k, and the irradiation strength $T_{tot}$ of all channels is that the sum of the preceding two complex numbers becomes the irradiation strength $T_{tot}$ of all channels. In a triangle which is formed by the three complex numbers 0, $T_k$, and $T_{tot}$, since the absolute value of $T_{tot}$ and the phases $\alpha_k$ and $\beta_k$ can be measured, the triangle can be determined, that is, $T_k$ can be obtained. The absolute value of $T_k$ can be obtained by the same expression as Expressions (6) and (7). This computation is performed for each pixel, thereby obtaining the B1 distribution of the channel k. The same computation is performed for all channels, and the B1 distribution of all channels can be obtained.

According to this embodiment, as in the first embodiment, the comparatively time-consuming B1 distribution measurement is performed only once, whereby it is possible to obtain the B1 distribution of all channels and to significantly reduce the B1 distribution measurement time as a whole. In this embodiment, since image data is acquired by irradiation with channels excluding only one channel, instead of obtaining image data for each channel, it is possible to reduce regions having small B1 in data and to achieve a high SN. Accordingly, the invention is suitable for B1 distribution measurement of a transmission coil having three or more channels.

In this embodiment, although a case where the image acquisition sequence in which irradiation with the (n−1) channels is performed is performed as the image acquisition sequence has been described, image data of the (n−1) channels may be synthesized from image data of one channel. In this case, as in the first embodiment, the image acquisition sequence in Step S200 performs the image acquisition sequence for each channel to obtain an image of each channel. In Step S210, prior to computation by Expressions (20) and (21), the images of the respective channels are synthesized to create the image of the (n−1) channels. The calculation of the B1 distribution of each channel using the image data, the image of all channels, and the B1 distribution is as described above.

Third Embodiment

That is, in the first embodiment and the second embodiment, although a case where, in Step S200 of the B1 distribution measurement, the image acquisition sequence 303 of all-channel irradiation is performed separately from the image acquisition sequence of individual channel irradiation has been described, in this embodiment, the image acquisition sequence of all-channel irradiation is omitted, and the all-irradiation image is synthesized using the images obtained in the image acquisition sequence of the individual channels. Hereinafter, description will be provided focusing on the difference from the first embodiment and the second embodiment.

Figure 7:
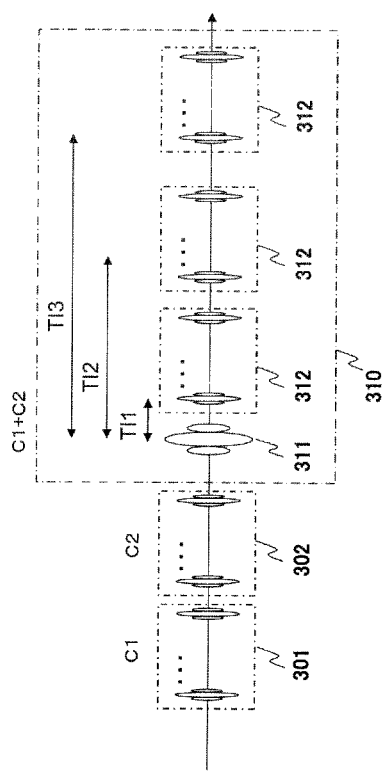
FIG. 7 is a diagram showing a pulse sequence for B1 distribution measurement in a third embodiment.

FIG. 7 shows an example of the pulse sequence which is executed in Step S200. In the drawing, the same elements as those in FIG. 4 are represented by the same reference numerals. Here, for simplification of description, although a case where the number of channels is two is described, the number of channels may be equal to or greater than three.

Figure 8:
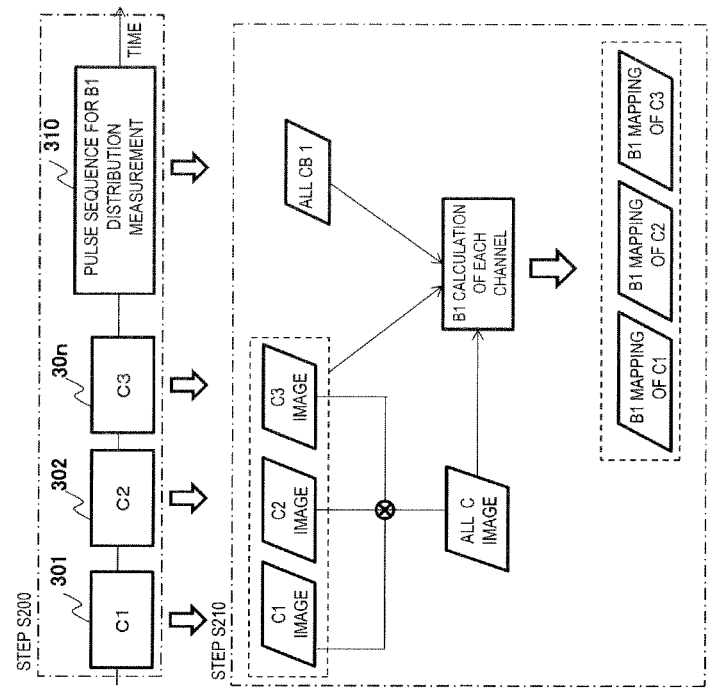
FIG. 8 is a diagram illustrating the concept of B1 distribution calculation in the third embodiment.

FIG. 8 conceptually shows S200 and S210 of this embodiment. FIG. 8 shows a case where the number of channels is three.

As shown in the drawing, in this embodiment, although the sequences 301, 302, and 30n in which images are acquired by irradiation with each of the channels C1, C2, . . . or by irradiation with the rest channels excluding one channel are executed, the image acquisition sequence of all-channel irradiation is omitted. Thereafter, the sequence 310 necessary for B1 distribution measurement is executed. In FIG. 7, although the pulse sequence 310 based on the multi-TI method is described as an example, the invention is not limited thereto.

As a result of these pulse sequences, the image (the image of the number of channels) of each channel or the (n−1) channels and multiple images having different TI obtained in the signal acquisition sequence 312 are obtained. In Step S210, as in the first and second embodiments, although the calculation of the B1 distribution of all-channel irradiation and the calculation of the B1 distribution of the individual channel are performed, in this embodiment, prior to these computations, the images of the respective channels are synthesized to obtain the image of all channels. The synthesis is performed by Expression (22) when obtaining the image $I_k$ of each channel or is performed by Expression (23) when obtaining the image $I_i$ of every (n−1) channels.

$$I_{tot} = \sum_{k=1}^{n} I_k \qquad (22)$$

$$I_{tot} = \frac{\sum_{i=1}^{n} I_i}{n-1} \qquad (23)$$

According to this embodiment, in Step S200, since the image acquisition sequence (303 of FIG. 4) of all-channel irradiation can be omitted, it is possible to reduce the time necessary for the pulse sequence for B1 distribution measurement.

Fourth Embodiment

This embodiment has a feature in that processing for dividing multiple channels into two sets and calculating the B1 distribution of each set is repeated until the number of channels constituting the set becomes one.

An image acquisition sequence which is introduced in this embodiment has a sequence in which, when multiple channels are divided into two groups and division is repeated until the number of channels after division becomes one, multiple images by irradiation using the channel groups and the channels of each division stage are acquired. In this case, the second irradiation magnetic field distribution calculation unit calculates the irradiation magnetic field distribution of each channel using image data of the channel groups, image data of the channels, and the all-irradiation image.

Figure 9:
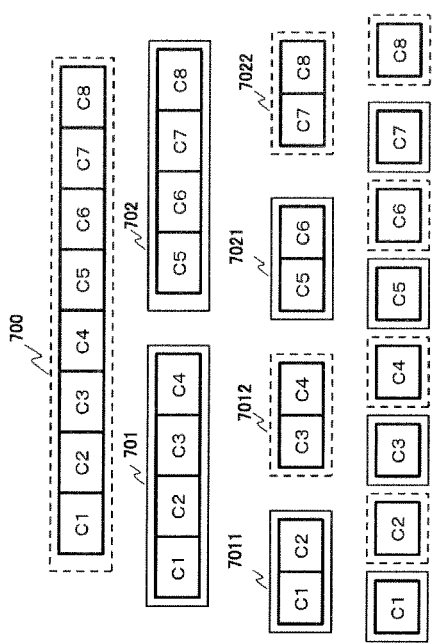
FIG. 9 is a diagram illustrating channel division in a fourth embodiment.

The outline of this embodiment is shown in FIG. 9 by way of an example where the number of channels is eight. Eight channels C1 to C8 are divided into two groups of a group 701 of the channels C1 to C4 and a group 702 of the channels C5 to C8, and for example, the B1 distribution of each of the channel groups 701 and 702 is measured in the same manner as in the first embodiment or the second embodiment. Each of the channel groups 701 and 702 is further divided into two groups, and similarly, the B1 distribution of each of the divided channel groups 7011, 7012, 7021, and 7022 is measured. Finally, this is repeated until the number of channels constituting a group becomes one.

Image data upon irradiation with all channels 700 before division can be obtained by synthesizing image data of the respective divided channel groups 701 and 702. With the initially divided groups 701 and 702 to the subsequent-stage divided groups, the B1 distribution of each of one group (7011) and the other group (7012) can be calculated from image data of the group (701) before division and image data of one group (7011) after division.

Accordingly, it is not necessary to perform the image acquisition sequence for all channel groups and channels, and the image acquisition sequence may be performed by half the number of divisions. In FIG. 9, a channel group or a channel in which image data is acquired by the image acquisition sequence is enclosed by a solid line, and a channel group or a channel in which image data acquisition by the image acquisition sequence can be omitted is enclosed by a dotted line. In Step S200, the image acquisition sequence using the channel groups or channels enclosed by the solid lines is performed, and in Step S210, the B1 distribution is calculated for each group as described above. The B1 distribution measurement of all-channel irradiation to be executed after the image acquisition sequence is the same as in the first and second embodiments.

In the first to fourth embodiments, although an embodiment in which the magnetic field strength T is calculated by Expressions (6) and (7) using the phase difference between the image (overall image) of all channels and the image (partial image) of one channel or the image (partial image) of the (n−1) channels has been described, in these embodiments, since phase information of the images is used for the B1 distribution calculation of each channel, precision is likely to be degraded in a region where the SN of the images is low. As will be understood from Expressions (6) and (7), when the phase difference "$\alpha-\beta$" or "$\alpha_k-\beta_k$" is close to 0 or $\pi$, the expression diverges, and the computation of the magnetic field strength using Expressions (6) and (7) is not possible. The following embodiment has a feature in that, in Step S310 which calculates the B1 distribution of each channel, means for preventing degradation of precision or divergence of computation in a region where the SNR of the images is low is provided.

That is, the arithmetic unit includes a determination unit which determines that the difference between the phase difference between the phase of one partial irradiation image and the phase of the overall image and the phase difference between the phase of another partial irradiation image and the phase of the overall image is equal to or greater than, or is equal to or smaller than a predetermined threshold value for each pixel.

In particular, the following fifth and sixth embodiments have a feature in that the arithmetic unit includes a determination unit which determines that the difference ($\alpha-\beta$ or $\alpha_k-\beta_k$) between the phase difference ($\alpha$ or $\alpha_k$) between the phase of a partial irradiation image of some channels and the phase of the overall image and the phase difference ($\beta$ or $\beta_k$) between the phase of a partial irradiation image of the other channels and the phase of the overall image is equal to or greater than, or is equal to or smaller than a predetermined threshold value for each pixel, and the recomputation of the irradiation magnetic field distribution is performed by the determination result of the determination unit.

Figure 10:
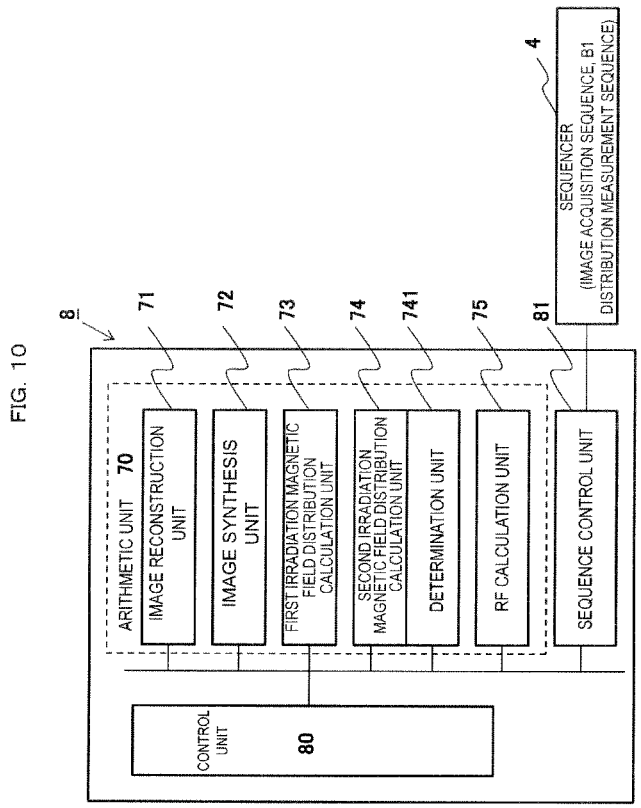
FIG. 10 is a functional block diagram of a control unit which is common to a fifth embodiment and a sixth embodiment.

FIG. 10 is a functional block diagram of the CPU 8 which is common to fifth and sixth embodiments. In the functional block diagram shown in FIG. 10, the same constituent elements as those in FIG. 2 are represented by the same reference numerals, and description thereof will not be repeated. As shown in the drawing, the arithmetic unit 70 includes a determination unit 741. The determination unit 741 determines whether or not B1 distribution calculation is possible with the SN of the images or the obtained phase differences between the images when the second irradiation magnetic field distribution calculation unit 74 calculates the B1 distribution of each channel on the basis of the phase differences between the images. As a result, when it is determined that precision of B1 distribution calculation is degraded with the SN of the images or computation of B1 distribution calculation diverges with the obtained phase differences, remeasurement or recomputation by the sequence control unit 81 or the first irradiation magnetic field distribution calculation unit 73 is performed through the control unit 80. Hereinafter, embodiments in which processing after the determination by the determination unit 741 is different will be described.

Fifth Embodiment

In this embodiment, as in the fifth embodiment, the determination unit 741 determines whether the value of the difference "$\alpha-\beta$" or "$\alpha_k-\beta_k$" between the phase differences is close to 0 or $\pi$. In this embodiment, when the difference is close to 0 or $\pi$ for a certain channel, the phase of the RF pulse to be irradiated for the channel changes to remeasure images.

Figure 11:
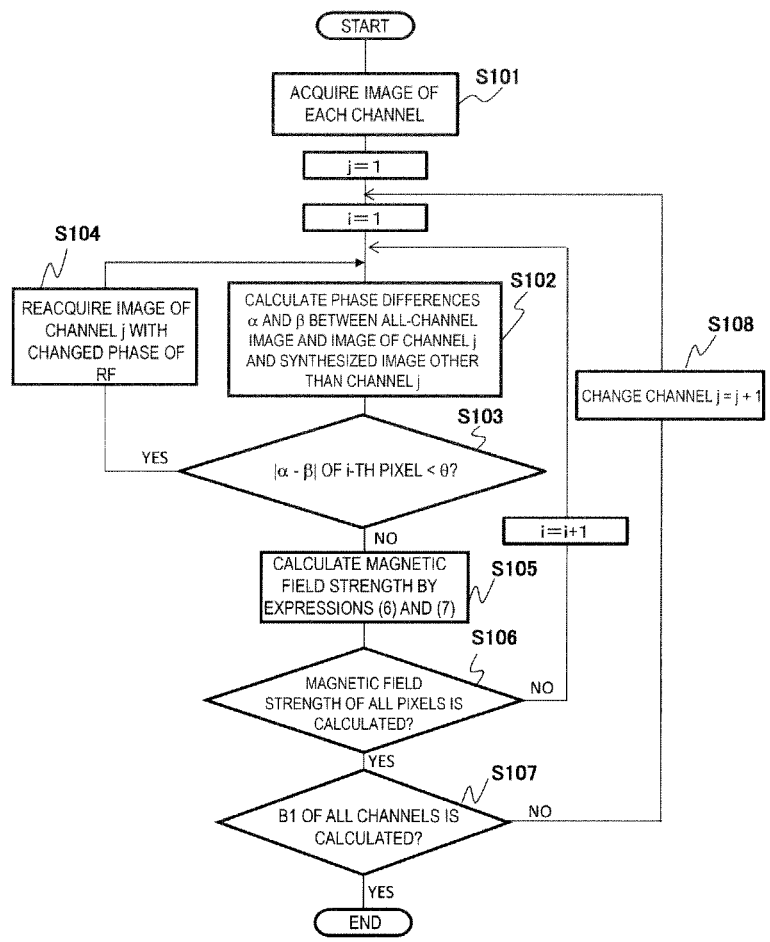
FIG. 11 is a flowchart showing a processing procedure of a fifth embodiment.

A processing procedure of this embodiment is shown in FIG. 11.

First, image data of each channel is acquired (Step S101) Image data may be image data of each channel as in the first embodiment, image data of the rest channels excluding one channel as in the second embodiment, or image data of each of two channel groups divided from all of the channels as in the fourth embodiment. Data in which the images of the multiple channels are synthesized may be used. Here, for simplification of description, a case where image data of each channel is used will be described as an example.

Next, the irradiation phase differences $\alpha$ and $\beta$ are obtained for each pixel using image data (partial irradiation image) of one channel, a synthesized image (partial irradiation image) in which images other than one channel are synthesized, and image data of all channels (Step S102). The difference or sum of the phase differences $\alpha$ and $\beta$ is obtained, and it is determined whether or not the value satisfies Expression (24) (Step S103).

$$|\alpha-\beta|<\theta \text{ or } \pi-\theta<|\alpha-\beta|<\pi+\theta \qquad (24)$$

(In Expression, $\theta$ is a threshold value set in advance)

As a result of the determination, when it is predicted that the phase difference $|\alpha-\beta|$ satisfies Expression (24) and magnetic field strength calculation fails, for the channel j which is a computation target in Step S102, the image is acquired again while differentiating the phase of the excitation RF pulse (Step S104). The RF phase during remeasurement is, for example, the phase during the first measurement $\pm\pi/2$.

In regard to the reacquired image of the channel j and the synthesized image of the channels other than the channel j, the phase differences $\alpha$ and $\beta$ from the phase of the all-channel image are recomputed for the pixels which satisfy Expression (24) (Step S102), and the magnetic field strength is calculated by Expressions (6) and (7) (Step S105).

After the irradiation magnetic field strength is calculated by Expressions (6) and (7) for all pixels (Step S106), the same processing is performed for other channels to obtain the B1 distribution of all channels (Step S107).

In Step S101, when acquiring image data of the rest channels excluding one channel, it should suffice that the same processing is performed by applying α and β to $α_k$ and $β_k$ of Expressions (20) and (21).

According to this embodiment, even when there is a region where the SN is low or even when the phase difference which causes the divergence of the expression is provided, it is possible to avoid divergence of the expression and to obtain the B1 distribution of each channel with high precision.

Sixth Embodiment

This embodiment has a feature in that a combination of channels for use in B1 distribution calculation changes depending on the determination result of the determination unit 741.

Figure 12:
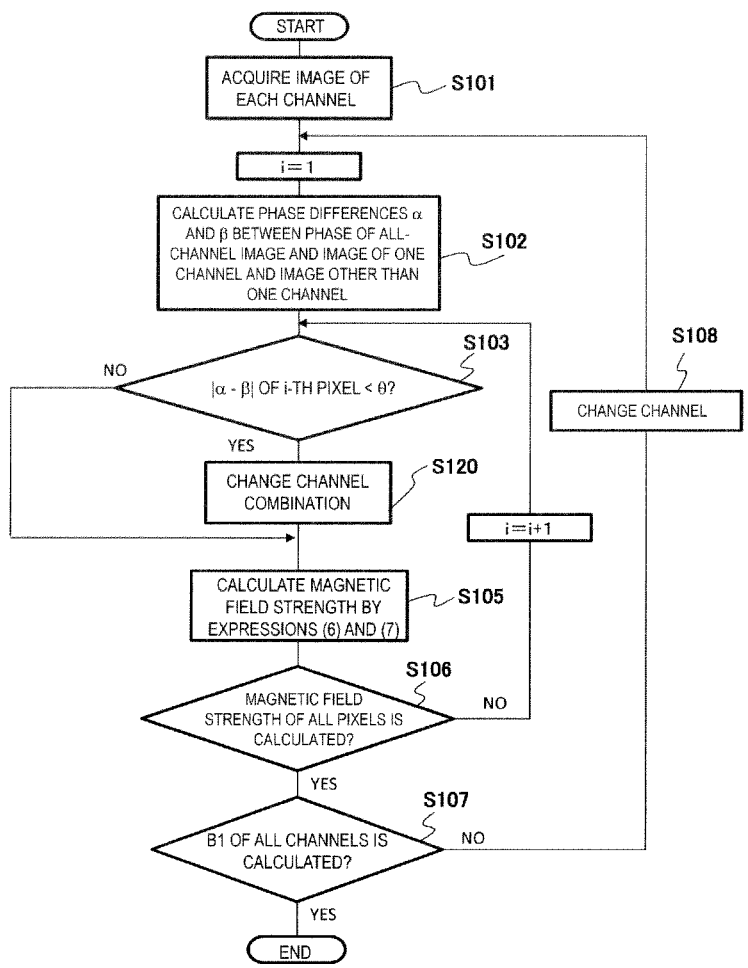
FIG. 12 is a flowchart showing a processing procedure of a sixth embodiment.
Figure 13:
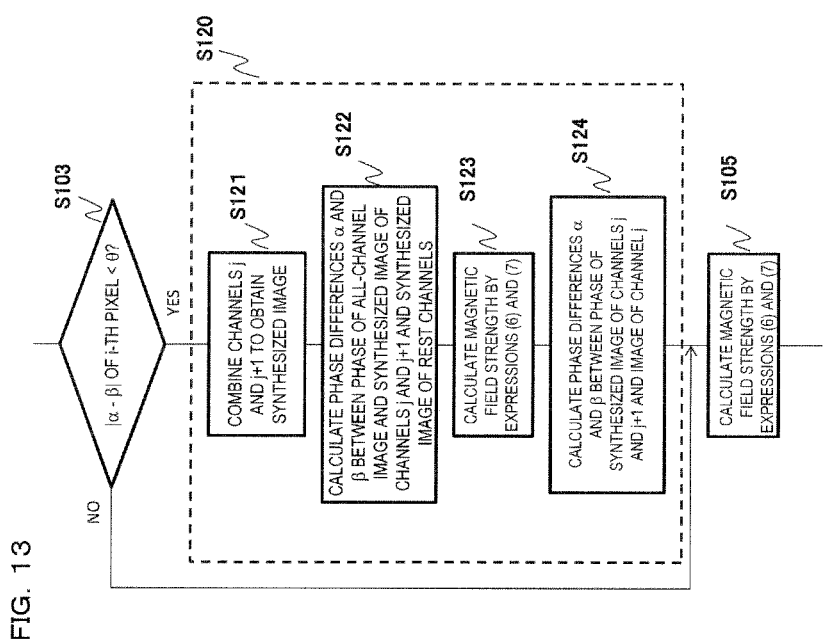
FIG. 13 is a flowchart showing a part of the processing procedure of FIG. 12.

A part of a processing procedure of this embodiment is shown in FIGS. 12 and 13. In FIG. 12, same steps as those in FIG. 11 are represented by the same reference numerals. This embodiment has a feature in that Step S120 is provided, instead of Step S104 (remeasurement step) of the fifth embodiment. FIG. 13 shows the details of Step S120 shown in FIG. 12.

In this embodiment, as in the fifth embodiment, the partial irradiation image of each channel and the synthesized image of the channels other than each channel are acquired (S101), the phase difference (α, β) between the phase of the all-channel image (overall image) and the phase of the partial irradiation image of each channel or the synthesized image is calculated (S102), and the determination of Expression (24) is performed (Step S103).

As a result of the determination by the determination unit 741, when it is predicted that the phase difference |α−β| satisfies Expression (24) and magnetic field strength calculation fails, computation using the image of one channel j and the image of the channels other than one channel is recomputed using the image of two channels (for example, j and j+1) and the image of the channels other than the two channels (Step S120). To this end, first, the image of two channels and the image of the channels other than the two channels are synthesized using the images of the respective channels acquired in Step S101 (Step S121). Next, for these two images, the phase differences from the phase of the overall image are calculated (S122), and the magnetic field strength upon irradiation with the two channels is calculated by Expressions (6) and (7) using these phase differences and the magnetic field strength upon irradiation with all channels (S123).

Figure 14:
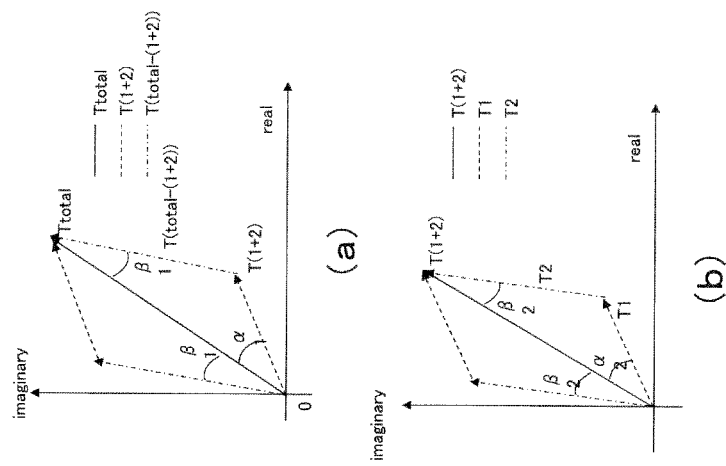
FIG. 14 is a diagram illustrating the concept of B1 distribution calculation in the sixth embodiment.

For example, when the magnetic field strength computation of the channel 1 in Step S103 diverges, as shown in FIG. 14(a), the magnetic field strength T(1+2) upon irradiation with the channels 1 and 2 is computed by Expressions (6) and (7) from the phase differences α1 and β1 between the images by irradiation with the channel 1 and the channel 2 and the overall image, and the magnetic field strength Ttotal upon irradiation with all channels.

The magnetic field strength upon irradiation with the two channels calculated in Step S143 is resolved into the magnetic field strength of the respective channels. Specifically, for example, as shown in FIG. 14(b), the differences α2 and β2 between the phase of the synthesized image of the two channels (here, the channel 1 and the channels 2 are illustrated) and both the phase of the image of the channel 1 and the phase of the image of the channel 2 are calculated (Step S124), and the magnetic field strength T1 of the channel 1 is computed by Expressions (6) and (7) using the phase differences α2 and β2 and the magnetic field strength T(1+2) upon irradiation with the two channels calculated in Step S143 (Step S105).

It should suffice that the computation in Step S140 is performed for pixels which are determined in Step S103 that Expression (24) is satisfied, and for other pixels, the magnetic field strength is computed directly in Step S105. Accordingly, even when pixels in which the magnetic field strength computation is determined to be failed are included, it is possible to calculate the magnetic field strength with high precision. Furthermore, since it should suffice that Step S140 for recomputation is performed for critical pixels, it is possible to prevent a significant increase in the amount of computation.

As in the fifth embodiment, Steps S101 to S108 and S120 are performed for other channels.

According to this embodiment, even when there is a region where the SN is low or even when the phase difference which causes the divergence of the expression is provided, it is possible to avoid the divergence of the expression, and to obtain the B1 distribution of each channel with high precision. However, since it is not necessary to perform recomputation, it is possible to reduce the total time of the B1 distribution measurement.

In the processing procedure of the MRI apparatus shown in FIG. 3, although the details of Step S200 in which the pulse sequence for B1 distribution measurement is executed and Step S210 in which the B1 distribution is calculated using data acquired in Step S200 have been described for each embodiment, various alterations or additions may be made to the respective embodiments. For example, the image acquisition sequence or the signal acquisition sequence may be a three-dimensional pulse sequence as well as a two-dimensional pulse sequence, and in this case, it is possible to acquire the B1 distribution having predetermined volume. In the foregoing embodiments, although a case where image data upon irradiation with all channels of the transmission coil having multiple channels and the B1 distribution are obtained has been described, all channels may not be all of the channels constituting the transmission coil, and the foregoing embodiment may also be applied to a case where multiple channels which constitute a part of the transmission coil are all channels, and the B1 distributions of the individual channels constituting the multiple channels are measured.

Next, imaging (main imaging) using the B1 distribution of each channel obtained as described above will be described.

During the main imaging, the control unit performs RF shimming using the irradiation magnetic field distribution calculated for each channel. Specifically, the control unit has a third image acquisition sequence (main imaging sequence) in which an image of an object is acquired, and the arithmetic unit includes a shimming unit which calculates a set of amplitude and phase of a high-frequency magnetic field to be irradiated in the third image acquisition sequence for each channel using the irradiation magnetic field distribution for each channel calculated by the second irradiation magnetic field distribution calculation unit.

Although an imaging procedure using the B1 distribution of each channel is the same as conventional imaging, hereinafter, the imaging procedure will be simply described, returning to the flow of FIG. 3.

Prior to imaging, the adjustment of an RF pulse using the B1 distribution calculated in Step S210 is performed. When the number of channels of the RF coil is n, the B1 distribution obtained for each channel is Blk(r), and the amplitude and phase of a high-frequency signal supplied to each small RF coil are Ak and φk, the magnetic field distribution B1$_{total}$(r) as a whole can be expressed by Expression (25).

$$B1_{total}(r) = \Sigma A_n \exp(i\varphi_n) B1_n(r) \quad (25)$$

A set of amplitude and phase which provides a homogenous magnetic field distribution B1(r) as the magnetic field distribution B1$_{total}$(r) (where r is the position of an actual space coordinate) is obtained while changing a set (Ak, φk) of amplitude and phase of Expression (25) (S220). This computation can be solved using a known nonlinear optimization algorithm, and for example, a set (Ak, φk) of amplitude and phase can be obtained using an optimization algorithm which minimizes the square root of a mean square error of B1$_{total}$(r) obtained by Expressions (25) and a target magnetic field distribution.

A set of obtained amplitude and phase is set in each small RF coil (a coil corresponding to one channel). Specifically, the amplitude and timing of the high-frequency pulse to be supplied to each channel of the RF coil are adjusted by the sequencer 4 and the modulator 12.

Desired imaging is performed using the set amplitude and phase, and an image is reconstructed (Steps S230 and S240). Since the B1 distribution measured in Steps S200 and S210 depends on the measured region of the object, when the object or the imaging region changes, the remeasurement of the B1 distribution is performed (S250). That is, the process returns to Step S200, and the measurement of the B1 distribution and the setting of the amplitude and phase of each small RF coil in conformance with the measurement result are performed. When there is no change of the region or when the movement of the region is movement to such an extent that the set amplitude and phase are used as they are, imaging is continued under the same irradiation conditions until imaging ends (S260). In this way, the B1 distribution measurement is performed only when the object or the imaging region changes, whereby it is possible to reduce the number of B1 distribution measurements and to improve throughput of examination.

EXAMPLE

Figure 15:
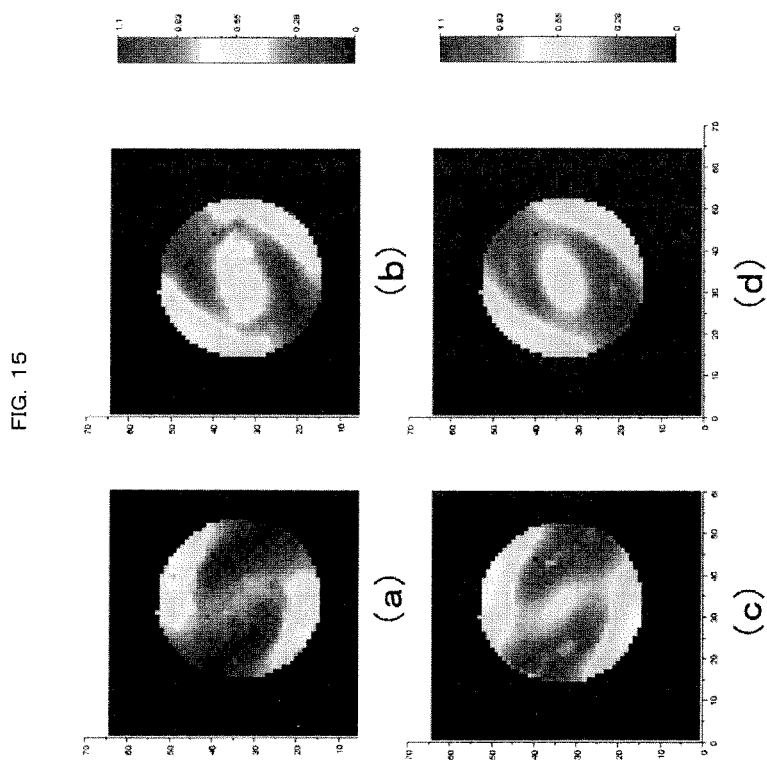
FIG. 15 is a diagram showing the result of an example.
Figure 16:
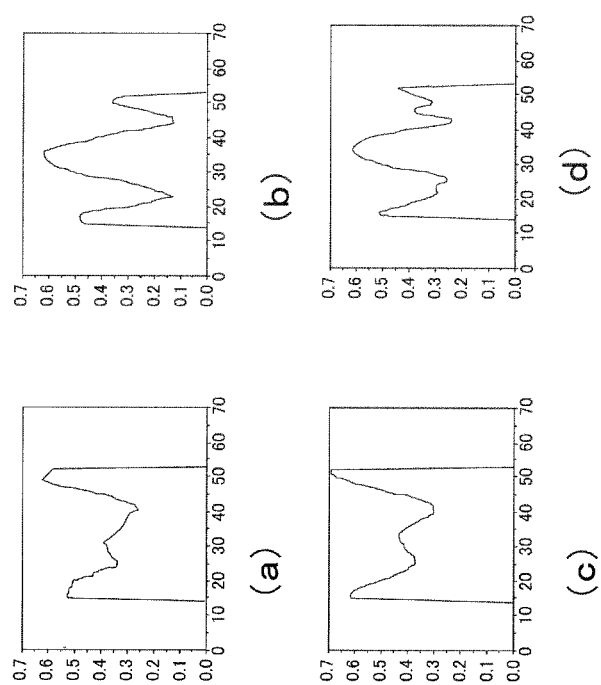
FIGS. 16(a) to 16(d) are diagrams showing line profiles of FIG. 15.

As an example, the B1 distribution measurement was performed by the method of the first embodiment using a two-channel transmission coil. As a comparative example, the same multi-TI method as the example was used, and the B1 distribution measurement for each channel was performed. The result is shown in FIGS. 15 and 16. FIG. 16 is a line profile of FIG. 15, and in the respective drawings, (a) and (b) show the result of the example and (c) and (d) show the result of the comparative example. In the comparative example in which the B1 distribution measurement for each channel was performed, while a computation error was large in a region having low B1, in the example, it was confirmed that the value of the region having low B1 was improved and precision was improved as a whole.

INDUSTRIAL APPLICABILITY

According to the invention, it is possible to perform the magnetic field distribution measurement (B1 distribution measurement) of the RF pulse in a very short time. Accordingly, since it is possible to perform the B1 distribution measurement and the control of the RF pulse based on the measurement result in real time with change of the imaging region, it is possible to reduce a burden on the object due to the extension of the imaging time, and in a high-magnetic field MRI which is likely to be influenced by the internal magnetic field of the object, to provide images having high diagnosability while eliminating the influence.

REFERENCE SIGNS LIST

2: magnetostatic field generation unit, 3: gradient magnetic field generation unit, 4: sequencer, 5: transmission unit, 6: reception unit, 7: signal processing unit, 8: CPU (arithmetic unit, control unit), 11: high-frequency oscillator, 12: modulator, 13: amplifier, 14a: high-frequency coil (transmission coil).

The invention claimed is:

1. A magnetic resonance imaging apparatus comprising:
an imaging unit which includes a transmission unit configured to irradiate a high-frequency magnetic field onto an examination target and a reception unit configured to receive a nuclear magnetic resonance signal from the examination target;
an arithmetic unit which processes the nuclear magnetic resonance signal acquired by the reception unit and performs an arithmetic operation including image reconstruction; and
a control unit which controls imaging by the imaging unit,
wherein the transmission unit includes a transmission coil having multiple channels, and
the control unit has
an image acquisition sequence in which an image is acquired by irradiation with one channel or a combination of two or more of the multiple channels, and
an irradiation magnetic field distribution measurement sequence in which an irradiation magnetic field distribution upon irradiation with all of the multiple channels is measured, and
the arithmetic unit includes
a first irradiation magnetic field distribution calculation unit which calculates the irradiation magnetic field distribution of all of the multiple channels using data acquired in the irradiation magnetic field distribution measurement sequence, and
a second irradiation magnetic field distribution calculation unit which calculates the irradiation magnetic field distribution of each channel of the multiple channels using multiple pieces of image data acquired in the image acquisition sequence and the irradiation magnetic field distribution of all of the multiple channels calculated by the first irradiation magnetic field distribution calculation unit, and
wherein the control unit has additionally a second image acquisition sequence in which an image of an object is acquired, and
the arithmetic unit includes a shimming unit which calculates a set of amplitude and phase of a high-frequency magnetic field to be irradiated in the second image acquisition sequence, using the irradiation magnetic field distribution calculated by the second irradiation magnetic field distribution calculation unit, for each channel of the multiple channels.

2. The magnetic resonance imaging apparatus according to claim 1,
wherein the second irradiation magnetic field distribution calculation unit calculates the irradiation magnetic field distribution of each channel using phase of an overall image acquired in one image acquisition sequence by irradiation with all of the multiple channels, phase of a partial irradiation image acquired in another image acquisition sequence by irradiation with some channels of the multiple channels, and the irradiation magnetic field distribution calculated by the first irradiation magnetic field distribution calculation unit.

3. The magnetic resonance imaging apparatus according to claim 1,
wherein the image acquisition sequence and the irradiation magnetic field distribution measurement sequence are the same pulse sequence.

4. The magnetic resonance imaging apparatus according to claim 1,
wherein the irradiation magnetic field distribution measurement sequence is one of the pulse sequences based on a double angle method (DAM), a fitting method, and an actual flip angle method (AFI).

5. The magnetic resonance imaging apparatus according to claim 1,
wherein the irradiation magnetic field distribution measurement sequence includes application of a high-frequency magnetic field pre-pulse by the transmission unit and multiple signal acquisition sequences having different elapsed times from the application of the high-frequency magnetic field pre-pulse.

6. The magnetic resonance imaging apparatus according to claim 1,
wherein the image acquisition sequence includes a pulse sequence in which irradiation with one channel of the multiple channels is performed, and the pulse sequence is repeated a number of times as a number of the multiple channels while changing the channels for use in irradiation, and
the second irradiation magnetic field distribution calculation unit calculates the irradiation magnetic field distribution of each channel using the image acquired for each channel and the image acquired by irradiation with all of the multiple channels.

7. The magnetic resonance imaging apparatus according to claim 1,
wherein the image acquisition sequence includes a pulse sequence in which irradiation with all other channels excluding one channel of the multiple channels is performed, and the pulse sequence is repeated the same number of times as the number of channels while changing a channel to be excluded, and
the second irradiation magnetic field distribution calculation unit calculates, using an image acquired with the pulse sequence excluding one channel and an overall image acquired in an image acquisition sequence by irradiation with all of the multiple channels, phase difference between phase of the image acquired with the pulse sequence excluding one channel and phase of the overall image and calculates the irradiation magnetic field distribution of each channel using the phase difference and the irradiation magnetic field distribution calculated by the first irradiation magnetic field distribution calculation unit.

8. The magnetic resonance imaging apparatus according to claim 1,
wherein the image acquisition sequence has a sequence in which, when the multiple channels are divided into two groups and division is repeated until a number of channels after division becomes one, multiple images by irradiation using the channel groups and all or some of the channels of each division stage are acquired, and the second irradiation magnetic field distribution calculation unit calculates the irradiation magnetic field distribution of each channel using image data of the channel groups and image data of the channels.

9. The magnetic resonance imaging apparatus according to claim 2,
wherein the arithmetic unit includes a determination unit which determines that a difference between (i) a phase difference between the phase of the partial irradiation image of said some channels and the phase of the overall image and (ii) a phase difference between phase of a partial irradiation image of remaining channels, other than said some channels, amongst the multiple channels, and the phase of the overall image is equal to or greater than, or is smaller than a predetermined threshold value for each pixel, and recomputation of the irradiation magnetic field distribution is performed based on a determination result of the determination unit.

10. The magnetic resonance imaging apparatus according to claim 9,
wherein, when the determination unit determines that the difference between the phase differences is smaller than the predetermined threshold value, the control unit repeats imaging by the imaging unit, and the arithmetic unit performs recomputation of irradiation magnetic field strength for pixels in which the difference between the phase differences is determined to be smaller than the predetermined threshold value.

11. The magnetic resonance imaging apparatus according to claim 9,
wherein, when the determination unit determines that the difference between the phase differences is smaller than the predetermined threshold value, the arithmetic unit changes a combination of channels of a partial image used in computation of the irradiation magnetic field distribution and performs recomputation of irradiation magnetic field strength for pixels in which the difference between the phase differences is determined to be smaller than the predetermined threshold value.

12. The magnetic resonance imaging apparatus according to claim 1, wherein the arithmetic unit includes an image synthesizing unit which synthesizes an image acquired from data of all of the multiple channels using multiple images each acquired by irradiation with some channels.

13. The magnetic resonance imaging apparatus according to claim 1, wherein the control unit executes the image acquisition sequence immediately before the irradiation magnetic field measurement sequence.

14. The magnetic resonance imaging apparatus according to claim 1, wherein the control unit executes the image acquisition sequence after TR of the irradiation magnetic field measurement sequence.

15. A method of measuring an irradiation magnetic field distribution of a transmission coil having plural channels of a magnetic resonance imaging apparatus, the method comprising:
an image acquisition step of, for multiple channels which are all or some of the plural channels of the transmission coil, performing irradiation using one channel or channels excluding at least one channel to acquire image data;
an irradiation magnetic field distribution acquisition step of acquiring an irradiation magnetic field distribution upon irradiation using all of the multiple channels;
an irradiation magnetic field distribution calculation step of calculating the irradiation magnetic field distribution of each channel of the multiple channels using image data acquired in the image acquisition step and the irradiation magnetic field distribution acquired in the irradiation magnetic field distribution acquisition step;

a second calculation step of calculating, using the irradiation magnetic field distribution calculated in the irradiation magnetic field distribution calculation step, at least one of amplitude and phase of a high-frequency magnetic field to be irradiated with each channel of the multiple channels; and a second image acquisition step of acquiring another image, by irradiating, with each channel of the multiple channels, the high-frequency magnetic field having said at least one of amplitude and phase calculated in the second calculation step.

16. The method according to claim 15, further comprising:

a step of performing irradiation using all of the multiple channels to acquire image data of all channels or a step of synthesizing image data of all channels using image data acquired in the image acquisition step.

\* \* \* \* \*